United States Patent
Arteta Montilva et al.

(10) Patent No.: US 11,955,243 B2
(45) Date of Patent: Apr. 9, 2024

(54) USING UNSTRUCTURED TEMPORAL MEDICAL DATA FOR DISEASE PREDICTION

(71) Applicant: Optellum Limited, Oxford (GB)

(72) Inventors: Carlos Federico Arteta Montilva, Oxford (GB); Nicholas Dowson, Oxford (GB); Timor Kadir, Oxford (GB); Jerome Declerck, Oxford (GB)

(73) Assignee: Optellum Limited, Oxford (GB)

( * ) Notice: Subject to any disclaimer, the term of this patent is extended or adjusted under 35 U.S.C. 154(b) by 381 days.

(21) Appl. No.: 17/094,949

(22) Filed: Nov. 11, 2020

(65) Prior Publication Data

US 2022/0148733 A1     May 12, 2022

(51) Int. Cl.
    *G16H 50/30*     (2018.01)
    *A61B 5/00*     (2006.01)
    (Continued)

(52) U.S. Cl.
    CPC ............. *G16H 50/30* (2018.01); *A61B 5/004* (2013.01); *A61B 5/055* (2013.01); *A61B 5/08* (2013.01); *A61B 5/7264* (2013.01); *A61B 5/7275* (2013.01); *A61B 5/7405* (2013.01); *A61B 5/742* (2013.01); *A61B 5/746* (2013.01); *A61B 5/7475* (2013.01); *A61B 6/032* (2013.01); *A61B 6/037* (2013.01); *A61B 8/00* (2013.01);
    (Continued)

(58) Field of Classification Search
    CPC ........ G16H 50/20; G16H 30/00; G16H 50/50; G16H 30/40; G16H 50/30; G16H 30/20
    See application file for complete search history.

(56) References Cited

U.S. PATENT DOCUMENTS

| 2012/0066001 A1 | 3/2012 | Sanborn |
| 2013/0089248 A1 | 4/2013 | Remiszewski et al. |

(Continued)

FOREIGN PATENT DOCUMENTS

| WO | 2019103912 A2 | 5/2019 |
| WO | WO-2022099303 A1 * | 5/2022 |

OTHER PUBLICATIONS

Xu, Yiwen, et al. "Deep Learning Predicts Lung Cancer Treatment Response from Serial Medical ImagingLongitudinal Deep Learning to Track Treatment Response." Clinical Cancer Research 25.11 (2019): 3266-3275. (Year: 2019).*

(Continued)

*Primary Examiner* — Jason B Dunham
*Assistant Examiner* — Constantine Siozopoulos
(74) *Attorney, Agent, or Firm* — Optimus Patents US, LLC

(57) ABSTRACT

A method for providing a lung disease risk measure in a Computer Aided Diagnosis system is described. The method comprising the steps of: receiving a plurality of inputs for a subject, each input comprising at least one image showing all or part of the lungs of a patient and a time stamp for the image, where the inputs are obtained at varying intervals; analysing the inputs to assess temporal changes in the images using at least one of an input data encoder and a time stamp encoder; inputting the output of at least one of the encoders to a score calculator to calculate a risk score; outputting the risk score indicating the lung disease risk for the subject. A Computer Aided diagnosis system for implementing the method is also described.

16 Claims, 5 Drawing Sheets

(51) Int. Cl.

| | |
|---|---|
| *A61B 5/055* | (2006.01) |
| *A61B 5/08* | (2006.01) |
| *A61B 6/03* | (2006.01) |
| *A61B 8/00* | (2006.01) |
| *G06T 7/00* | (2017.01) |
| *G16H 10/40* | (2018.01) |
| *G16H 30/20* | (2018.01) |
| *G16H 30/40* | (2018.01) |
| *G16H 50/20* | (2018.01) |
| *G16H 50/50* | (2018.01) |
| *G16H 50/70* | (2018.01) |

(52) U.S. Cl.
CPC ........... *G06T 7/0016* (2013.01); *G16H 10/40* (2018.01); *G16H 30/20* (2018.01); *G16H 30/40* (2018.01); *G16H 50/20* (2018.01); *G16H 50/50* (2018.01); *G16H 50/70* (2018.01); *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/10132* (2013.01); *G06T 2207/20081* (2013.01); *G06T 2207/20084* (2013.01); *G06T 2207/30061* (2013.01)

(56) References Cited

U.S. PATENT DOCUMENTS

| | | | |
|---|---|---|---|
| 2019/0130565 A1* | 5/2019 | Lee | G06T 7/30 |
| 2022/0039768 A1* | 2/2022 | Wang | A61B 5/7267 |
| 2022/0051771 A1* | 2/2022 | Lyman | G06T 7/0014 |

OTHER PUBLICATIONS

Causey, Jason L., et al. "Highly accurate model for prediction of lung nodule malignancy with CT scans." Scientific reports 8.1 (2018): 1-12. (Year: 2018).*
End-to-end lung cancer screening with three-dimensional deep learning on low-dose chest computed tomography Diego Ardila, Atilla P. Kiraly, Sujeeth Bharadwaj, Bokyung Choi, Joshua J. Reicher, Lily Peng, Daniel Tse, Mozziyar Etemadi, Wenxing Ye, Greg Corrado, David P. Naidich, and Shravya Shetty.
Recommendations for Measuring Pulmonary Nodules at CT: A Statement from the Fleischner Society Alexander A. Bankier, MD, Phd Heber MacMahon, MB, BCh Jin Mo Goo, MD, Phd Geoffrey D. Rubin, MD Cornelia M. Schaefer-Prokop, MD, PhDDavid P. Naidich, MD.
British Thoracic Society guidelines for the investigation and management of pulmonary nodules M E J Callister, D R Baldwin, A R Akram, S Barnard, P Cane, J Draffan, K Franks, F Gleeson, R Graham, P Malhotra, M Prokop, K Rodger, M Subesinghe,D Waller, I Woolhouse, British Thoracic Society Pulmonary Nodule Guideline Development Group, on behalf of the British Thoracic Society Standards of Care Committee.
Optimisation of volume-doubling time cutoff for fast-growing lung nodules in CT lung cancer screening reduces false-positive referrals. Volume doubling time of lung cancers detected in a chest radiograph mass screening program: Comparison with CT screening Maki Kanashiki, Takuji Tomizawa,, Iwao Yamaguchi, Koichi Kurishima, Nobuyuki Hizawa, Hiroichi Ishikawa, Katsunori Kagohashi, and Hiroaki Satoh.
Lung RADS Assessment Categories.
Guidelines for Management of Incidental Pulmonary Nodules Detected on CT Images: From the Fleischner Society 2017.
EP Application No. 21206440.6 to Optellum Limited, EPO Article 94(3) Communication, Jan. 18, 2024.

* cited by examiner

USING UNSTRUCTURED TEMPORAL MEDICAL DATA FOR DISEASE PREDICTION

FIELD OF INVENTION

This invention relates to the field of Computer Aided Diagnosis systems and methods for assisting the interpretation of medical images to support clinicians in their practice. In particular, the field relates to risk Computer Aided Diagnosis systems to assist the reading and reporting of medical images by radiologists and the interpretation of the radiologist's report by the physician responsible for patient care.

BACKGROUND OF INVENTION

In the field of medical imaging, a variety of technologies can be used to investigate biological processes and anatomy. The following examples are types of scan that may be used to provide medical images: X-Ray; Computed Tomography CT; Ultrasound US; Magnetic Resonance Imaging MRI; Single Photon Emission Tomography SPECT; and Positron Emission Tomography PET. Each type of scan is referred to as an "imaging modality".

Typically, an image scan provides a "dataset". The dataset comprises of digital information about the value of a variable at each of a plurality of spatial locations in either a two- or three-dimensional space, for example, a CT scan may provide a 3D image of the chest of a patient. Such datasets are also known as 3D medical images.

Lung cancer remains the most common cause of cancer-related death in the UK and USA, even though lung cancer is usually curable if caught at an early stage. As a result of recent lung cancer studies, including the National Lung cancer Screening Trial NLST and the Dutch-Belgian Randomized Lung Cancer Screening Trial with the Dutch acronym NELSON, the large scale screening of patients using Computed Tomography CT is now being considered for roll-out by national health organisations. For example, in some areas of the UK, the National Health Service NHS is currently enrolling over 55s who are ex-/current smokers for the 'Lung Health Check' program. In the program, those people with abnormally low lung function, say as assessed by spirometry, receive a CT scan. A CT scan is performed by a machine that analyses how much X-Rays are absorbed by the body when emitted from different angles to generate the CT, which is a three-dimensional 3D reconstruction of the different tissues of the patient. The CT can also be referred to as a medical image, although this term is broader, in that it can also refer to images generated by other scanners, such as Magnetic Resonance Imaging MRI, Positron Emission Tomography PET, which are also sometimes used to aid in diagnosing lung cancer. In addition to screening programs, CT scans are often taken of the chest to check for broken bones or investigate the causes of the symptoms of disease, such as a persistent cough, shortness of breath, chest pain or fever. In addition to any other diseases such as Bronchiectasis or Chronic Obstructive Pulmonary Disease COPD, the CT is also examined to check for lung nodules. Patients in whom suspicious lung nodules are identified then undergo a biopsy or follow-up imaging, in order to check whether the lung nodules are cancerous.

Radiologists and other clinicians can assess the images in the visible anatomical regions, considering both normal tissue and any lesions within a person. The assessment can be performed with the assistance of computer aided detection CADe systems. CADe systems serve to detect and highlight suspicious regions that may have been missed by a radiologist if they hadn't been using the CADe system. During the examination of the CT a related task referred to as Computer Aided Diagnosis CADx can be performed to aid in the diagnosis of detected abnormalities. CADx systems attempt to assist the clinician in classifying any findings correctly, and typically rely on the user to identify and provide the abnormalities for subsequent classification. For example, if a radiologist has identified a lung nodule in a CT scan, the CADx system can provide a score that is indicative of the risk of malignancy to assist the clinician in classifying the identified lung nodule as either a potentially malignant tumour or a benign finding. Despite the numerous examples of CADx in the academic literature, few CADx systems are available commercially, because there are many challenges associated with deploying practical systems. An example of a commercial CADx system is the Transpara™ product from Screenpoint™ for breast cancer characterisation from X-Ray mammograms.

The outcome of an assessment may not be a clear diagnosis such as "benign" or "malignant". For example, in the context of lung nodules found within an incidental CT or a first CT from a screening program, diagnoses are usually not definitive. In the case of an unclear finding, at least one follow-up CT after an intervening period may be required to clarify whether a nodule is malignant or not. The passage of time allows observable changes in the nodule to become apparent, which can supply additional evidence for a more definitive clinical diagnosis. Therefore, consideration of the changes in nodule appearance over a period of time is recommended for assessing and managing pulmonary nodules. For instance, observed growth in a lung nodule over a three-month period can be a strong indicator of potential malignancy, while a solid nodule remaining the same size for two years is a typically considered to indicate benignity. A similar scenario can be seen in other clinical contexts such as breast cancer screening.

Clinicians can consider different manifestations of change in the presentation of lung nodules, for instance, change in size, the appearance of solid components in a non-solid nodule or changes in appearance at the edge of the nodule. Growth is a particularly important factor for discriminating between benign and malignant nodules, and commercial products such as Philips™ Intellispace™ and GE™ Lung VCAR™ are available to measure and present the growth of lung nodules. Popular measures of growth include volume doubling time VDT and change in diameter [Bankier]. The use of VDT is explicitly suggested in some clinical guidelines [3] for making management decisions for pulmonary nodules. However, measuring VDT requires specialised software, so [Bankier] suggests measuring the nodule diameter using electronic callipers. Diameter measurements suffer from reader variability, hence [Bankier] recommends that growth in diameter not be treated as definitive unless it exceeds 2 mm. Automatic measurements of volume are also variable. An over-estimation in the size of a nodule can result in a false positive finding. A false positive occurs when a nodule is in fact benign but is assumed to be potentially malignant and can result in an unnecessary biopsy or surgical procedure being performed, which can put the patient at risk of an adverse event. In contrast, false negatives occur when a cancer is missed during the assessment of a medical image. False positives are of sufficient concern that it has been proposed that the VDT thresholds, above which nodules are considered to be suspicious, should be adjusted to reduce false positives even if it means missing slow growing cancers. Another important cue for malignancy is the appearance or growth of solid components in non-solid nodules. Nevertheless, this measure can be more subjective than nodule growth, and it should only be applied to non-solid nodules.

There is a more fundamental limitation to current clinically accepted measures of change in nodules: the measure of a single parameter might not offer enough discrimination between malignant and benign nodules. Instead, more discriminative models should account for non-trivial, but meaningful, patterns in the data that are difficult to express and quantify by humans. For instance, changes in the appearance of nodule spiculations, which are long tendril-like structures extending away from the nodule edge, could be informative but difficult to quantify in a manner that is reproducible across medical practitioners.

Machine learning models such as neural networks represent a good alternative to measuring nodule changes in terms of single, human-defined parameters. These models can learn, directly from data, what patterns of change in the nodule images to consider such that the discrimination between benign and malignant nodules is maximised.

A state-of-the-art machine learning model under this paradigm of automated CADx systems has been described in the recent academic publication [Ardila et al] by researchers at Google. This model not only predicts cancer risk from a single CT image, but can also incorporate information from a previous CT scan while eschewing the explicit measurement of changes of volume or any other predefined parameters.

The Google model has been designed for lung cancer screening programs, with the main goal of predicting the likelihood that a patient will develop cancer before the next scan. Consequently, it assumes that patients are scanned at regular time intervals, following the current practice of annual scans. This rigid assumption about the temporal information is suitable for screening programs or other controlled settings where the patients are expected to follow a fixed testing schedule. However fixed scanning intervals are not typical for pulmonary nodules. Many pulmonary nodules are not discovered within screening programs but are rather discovered incidentally when the patient is being investigated for diseases such as heart disease or a broken bone.

Once a nodule is detected and deemed to be suspicious, whether it comes from a screening program or an incidental finding in a clinic, it is then the responsibility of a clinician to decide on the appropriate next step. Once a nodule has been deemed suspicious enough to require closer management by a clinician, the time interval before a follow-up study is performed can vary substantially. Time intervals can range from several days if the case is urgent and a better quality CT is needed, to one month to discount inflammatory conditions or three, size, or twelve months depending on the clinician's assessment of the risk of cancer. The clinician may also require further follow-ups. Therefore, follow-up studies for nodules under clinical management vary in how many studies are needed and the interval between CT scans.

REFERENCES

Ardila et al. 2019 "End-to-end lung cancer screening with three-dimensional deep learning on low-dose chest computed tomography"
Bankier, et el. 2017 "Recommendations for Measuring Pulmonary Nodules at CT"

SUMMARY OF THE INVENTION

Accordingly, the invention seeks to mitigate, alleviate or eliminate one or more of the abovementioned disadvantages singly or in any combination.

In an embodiment of the invention there is provided a method for providing a lung disease risk measure in a Computer Aided Diagnosis system comprising the steps of: receiving a plurality of inputs for a subject, each input comprising at least one image showing all or part of the lungs of a patient and a time stamp for the image, where the inputs are obtained at varying intervals; analysing the inputs to assess temporal changes in the images using at least one of an input data encoder and a time stamp encoder; inputting the output of at least one of the encoders to a score calculator to calculate a risk score; outputting the risk score indicating the lung disease risk for the subject. In a preferred embodiment of the invention the lung disease is lung cancer.

In an embodiment of the invention each variable interval between inputs is up to 3 years. Preferably, the variable interval between inputs is between 1-18 months. Further preferably, the variable intervals between each input of the plurality of inputs are all different.

In an embodiment of the invention each of the plurality of inputs is processed by the input data encoder to determine patterns in the inputs. Further preferably, the input data encoder will encode the result of the input processing as an input data descriptor.

In a further embodiment of the invention the output from at least one encoder is provided to a system state calculator, and the system state calculator encodes a summary of all the input data received at that time. Preferably, the system state calculator calculates the current risk score based on input data it has received between an initial starting point with zero input to the system state calculator and a point when at least one input of a plurality of inputs has been provided to the system state calculator.

In an embodiment of the invention, the system state calculator is updated via a feedback system, to take account of data from successive images.

In an embodiment of the invention, the mothed further comprising the step of: detecting a rare system state, and outputting an alert with the risk score to indicate the detected rare state.

Preferably, the input image is one of: a CT image, an MRI image, a PET image, an X-ray image, an ultrasound image or a SPECT image.

In a preferred embodiment of the invention, the input further comprises one of more of: biomarkers for the patient or clinical parameters for the patient. Preferably, the biomarkers and clinical parameters comprise at least one of: patient age, patient sex, results of blood tests, results of lung function tests.

In a further embodiment of the invention, the step of analysing the inputs is done with a machine learning model. Preferably, the machine learning model uses a neural network. Further preferably, the neural network is a recursive neural network.

In an embodiment of the invention the output is an textual, visual or audio output.

According to the invention there is also provided a computer aided diagnosis lung disease risk measurement system comprising: an input circuit for receiving a plurality of inputs for a subject, each input comprising at least one image showing all or part of the lungs of a patient and a time stamp for the image, where the inputs are obtained at varying intervals; an analysis circuit comprising at least one of an input data encoder and a time stamp encoder for analysing the inputs to assess temporal changes in the images using at; said analysis circuit further comprising to a score calculator for receiving the output of at least one of the encoders to calculate a risk score; an output circuit for outputting the risk score indicating the lung disease risk for the subject.

In a preferred embodiment of the invention, the computer aided diagnosis system further comprising: a circuit configured for the detection of rare system states to determine a rare system state and wherein the output circuit also comprised an alert mechanism, to provide an alert along with the disease risk output when the rare system state is determined. Preferably, the circuit configured for the detection of rare system states evaluates the likelihood of a system state and compares this with a threshold level to determine the rare system state and to generate the alert.

The difference between the temporal structure of the data coming from a fixed setting e.g. a screening program which will see patients and obtain image scans at regular fixed intervals and those under clinical management, represent an important technical challenge for CADx systems that aim to predict the risk of lung disease, such as lung cancer for example, using temporal data.

We refer to these two types of temporal sequences as i fixed temporal data, for those sequences of pre-specified time-interval between data points and a fixed sequence length where the interval between all data points is always the same, and ii unstructured temporal data, for those sequences with variable time-interval between studies and variable sequence length. For a CADx system to be used in common clinical practice, it must be able to handle unstructured temporal data. That is, it must have the flexibility to parse a sequence of studies of unknown length while explicitly considering the variable time between studies. Note that fixed temporal data is a special case of unstructured temporal data, thus a CADx system able to operate on unstructured data would also be applicable to scenarios with fixed temporal data.

There is a need for a CADx system for disease risk assessment in lung nodules that can operate on unstructured temporal data. Preferably, the disease would be lung cancer.

This invention allows a CADx system for the diagnosis of lung disease, preferably the diagnosis of lung cancer to use the valuable temporal information available in the unstructured temporal sequences that are typically acquired when lung nodules come under clinical management, and image scans can be acquired over a range of different intervals.

Nodules enter clinical management either because they are discovered incidentally or are discovered during a screening program and are considered to have a non-negligible risk of being malignant. Screening programs typically specify the number of scans that are performed and the time interval between scans. In a preferred embodiment of the invention the scan would be a CT scan, but other imaging modalities may also be possible within the scope of the invention. However, once nodules require clinical management, a physician decides on what follow-up studies are required and when they should be scheduled. Hence, unlike screening studies, sequences of studies collected during clinical management occur within variable time intervals and a variable number of times.

The proposed invention can be used both for nodules within screening programs and once patient with nodules enter clinical management programs. This is possible, because the CADx system for unstructured temporal data recognizes the limitations of previous systems when handling temporal information and overcomes them by allowing the explicit encoding of a time stamp associated to every study in a way that can be used by a machine learning model to account for the variability in the time interval between subsequent data points.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION

Overview of the CADx System for Unstructured Temporal Data

Figure 1:
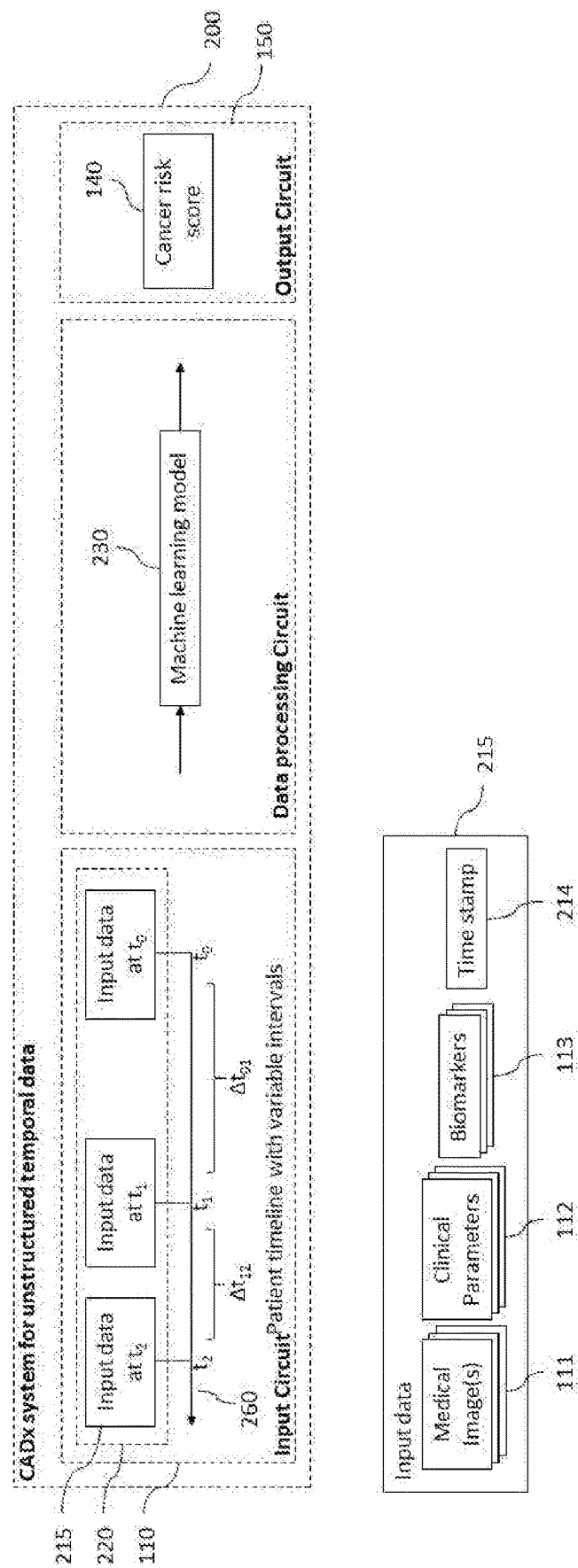
FIG. 1 illustrates a CADx system according to an embodiment of the invention.

FIG. 1 shows the CADx 200 system according to an embodiment of the invention. The CADx system uses unstructured temporal data 200 that is not limited in the temporal structure of the input data. Instead, the invention uses a flexible temporal structure 260 is permitted where the sequence of input studies is not constrained in its length. Also, in the preferred embodiment of the invention, the time interval where $\Delta t_{nm}$ is the interval between input n and input m between input studies does not need to be pre-specified and can vary between subsequent input data points. In a preferred embodiment of the invention there are no minimum or maximum limits on the time intervals between input points.

As shown in FIG. 1, first input data is provided at $t_0$, then after time interval $\Delta t_{01}$ another input data is provided at time $t_1$. Then interval $\Delta t_{12}$ passes, and then more input data is provided at $t_2$. The interval between each input data is variable. In an embodiment of the invention, the interval between input data points maybe up to 3 years, in a preferred embodiment the interval is between 1 to 18 months. Preferably, the intervals are all different time periods, however in certain embodiments of the invention, it is possible that some of the intervals may be the same, as long as the overall intervals are variable, and there is no structure to the intervals.

This input sequence of studies 220 with these characteristics is referred to as unstructured temporal data. A unit of unstructured temporal data 215 may also include the time stamp 214 of the study with which it is associated.

A unit of input data 215, corresponding to a single date when an image was acquired, contains at least one image scan 111, in an embodiment of the invention this may be provided in combination with one or more clinical parameters 112 such as patient age and sex, and the result of one or more relevant tests such as biomarkers 113, or a test for a gene mutation associated with an increased risk of cancer examples of the biomarkers, as well as functional results, such as lung function test for example. All data in an input data 115 is assumed to have been collected to gather evidence regarding lung disease risk. In a preferred embodiment of the invention the lung disease is lung cancer. Preferably the image scan is a CT scan, but other imaging modalities may also be used to produce the scan.

When an input sequence 220 is presented to the machine learning model 230, the model performs a sequential series of mathematical operations on the values in the input data, the result of which is a lung disease risk score 140. The risk score is then provided via the output circuit 150. Preferably, the output can be provided as text, or an image, or some other visual, graphical, textual or audio output. Preferably, the numerical output can be provided as text with an accompanying plot that provides some context for the user to interpret the number. For example the output may be an integer ranging from 1 to 10 and have an accompanying plot to show that within the population of incidentally found nodules, of those nodules with the score shown a certain percentage are malignant. The output could also be provided as text on its own, or an image, or some other visual textual or audio output."

In the preferred embodiment of the invention, the machine learning model 230 in the CADx system for unstructured temporal data 200 is trained to parse the flexible temporal structure in the input sequence 215 in order to produce a lung disease risk score 140 for the patient providing the input data.

The temporal variability allowed in the input sequence 215 of a CADx system for unstructured temporal data is what permits the usage of temporal information coming from the real pathway that lung nodules follow when under clinical management. That is, once a nodule is detected in any setting, e.g. an incidental finding or in a screening program, the scheduling of potential subsequent studies, as well as the number of subsequent studies, will depend on the clinical decision making of the managing clinician instead of a pre-defined schedule, thus the inputs will be variable. Therefore, a system that assumes a fixed structured of the temporal data, with no variability between the input data would be unable to make use of the temporal information that becomes available during the nodule management process. The CADx system 200 of this invention for unstructured temporal data can process such variable sequences, considering all of the temporal data available at a given time, regardless of the variability between the intervals when the data was obtained.

A typical use for the CADx system 200 for unstructured temporal data is described in the following example. A patient visits a healthcare provider for a cardiac exam involving a CT scan that will cover the area of the thorax. Incidentally, a suspicious lung nodule is spotted in the CT image, and the managing clinician decides to use the risk assessment tool help them choose the most appropriate care pathway for the nodule. At this point in time, the nodule's appearance on the collected image does not provide clear information, thus the clinician decides to schedule a follow-up visit for three months later. At the follow-up visit, a second CT scan is obtained. As before, the managing clinician seeks the support of the malignancy evaluation system, only this time the system will take both CT scans and the variable time interval between them into consideration. The CADx system 200 can now assess temporal changes in the nodule, such as growth and changes in morphology, and update its previous risk assessment of the nodule. This process can be repeated for as long as the nodule continues to be monitored, adding further information with every new study. A typical lung nodule follow-up interval is 3, 6, or 12 months but sometimes patients can obtain a new CT a few days later if the case is urgent and a higher quality CT is needed, or a month later if a cross-diagnosis for an infection is required, or more than a year later if the patient misses their follow-up.

Background on Machine Learning Models

The mathematical operations in the machine learning models are controlled by a set of model parameters. The choice of mathematical operations and the order in which they are performed are referred to as the model architecture. The model parameters are worked out in a process known as model training, so that they can identify patterns that occur in the input data whose presence is informative for the prediction task that the CADx system performs. As used in regard to this invention, the term pattern refers to certain arrangements of the values in the input data that are informative for the task being performed, for example predicting whether a nodule is malignant or benign. Internally to the machine learning model, the mathematical operations are divided into groups of operations (there is no maximum group size, the minimum group size is 1) that are referred to as features. Each feature is sensitive to a particular set of patterns. When an input is presented to the model each feature responds to the set of patterns in the input data and outputs a value known as an activation. In an embodiment of the invention, the model combines the feature activations using another mathematical function, for example a weighted sum, to produce the model output. For instance, in a CADx system for predicting whether a lung nodule is malignant or benign the model output would be a cancer risk score 140.

Training of a machine learning model requires a set of input data, where each datum is associated with one or more values collectively referred to as labels. For instance, in a dataset comprising of 10,000 CT images each with a cancer diagnosis indicated by the value zero or one and a smoking history indicated by a non-zero value in packyears, the diagnosis and smoking history are labels. Medical data is often inaccurate or incomplete, hence if the labels are to be used to train or evaluate a model they need to be sufficiently accurate. When labels for the images have been verified to be accurate, they are referred to as ground-truth labels.

During training of a machine learning model, the model parameters are preferably automatically adjusted by an optimization algorithm. The optimization algorithm measures how well the machine learning model performs at the task and works out what changes to the machine learning model parameters are needed to make the machine learning model perform better. The optimisation of the model is repeated until the model performs well on another set of data that is not used for training of the model. An example of a task for the machine learning model is discerning benign from malignant nodules from CT images, or images of other modalities, where model performance is measured using a label for cancer diagnosis that is associated the images.

Example Implementation of the CADx System for Unstructured Temporal Data

Figure 2:
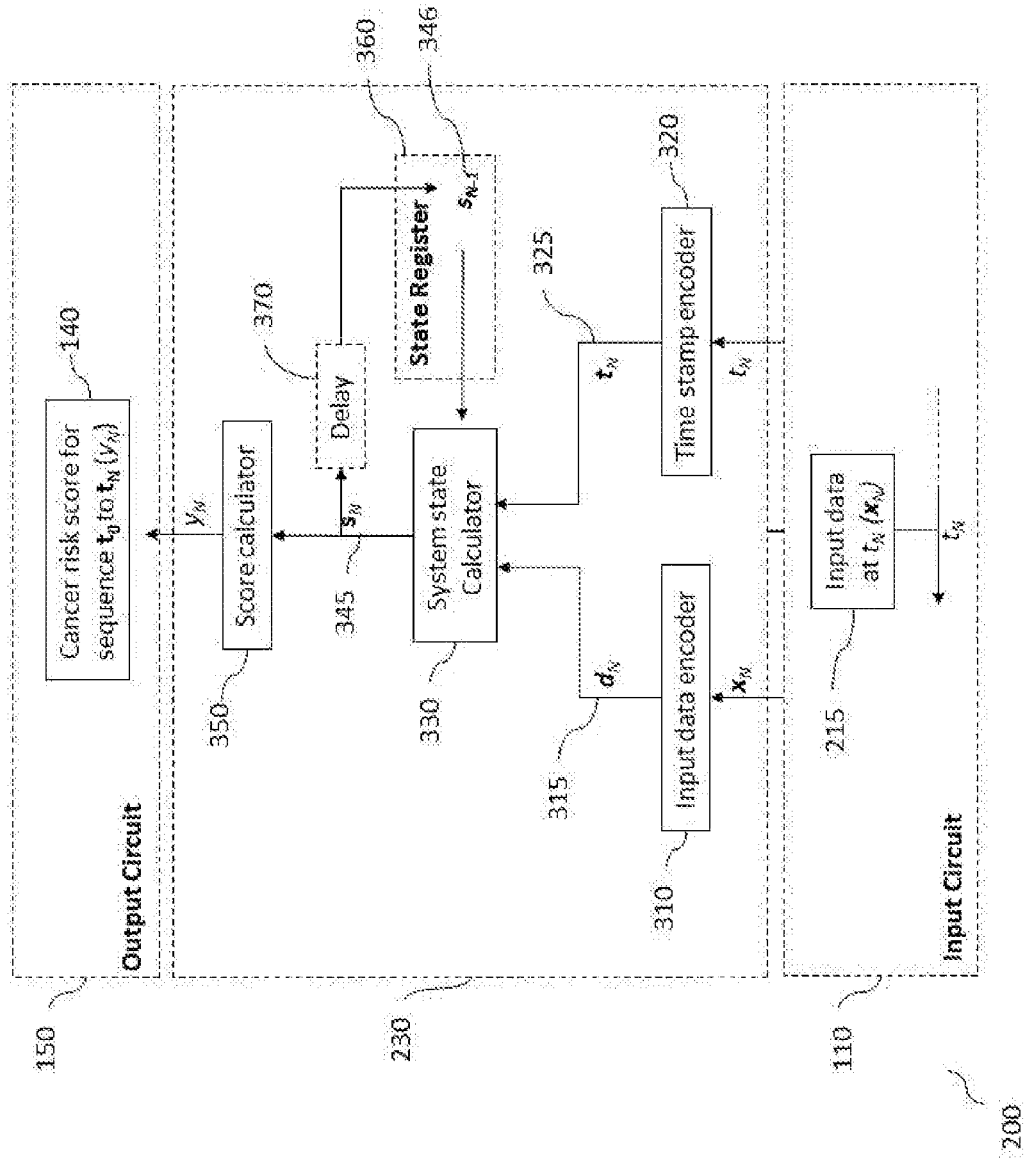
FIG. 2 show a high-level implementation of the CADx system for unstructured temporal data

An example of a high-level implementation of the CADx system for unstructured temporal data 200 according to an embodiment of the invention is shown in FIG. 2. This shows an input circuit 110, output circuit 150 and the machine learning model 230.

Each input data unit 115 in the input sequence 220, $x_N$, corresponding to one imaging study performed on one day using a defined imaging modality, is first processed by an input data encoder 310 which identifies the presence of relevant patterns present in any of the input data 111, 112, 113 apart from the time-stamp 214 and encodes the result the presence of the patterns as a collection of feature activations referred to as the input data descriptor 315, $d_N$, where N is a whole number representing how many input elements have been presented to the system so far.

The information regarding the time of the study, $t_N$, 214 is parsed by a time stamp encoder 320, which encodes the time information in a way that can be used by the rest of the system, typically as at least one numerical value stored in a vector, $t_N$ 325. The two descriptors, the input data descriptor and the time stamp descriptor 315, 325 are supplied to a system state calculator 330, whose output is a current system state 345, which comprises of a collection of one or more values typically stored as a vector of numerical values, $s_N$. The system state 345 encodes a summary of all the input data units 215 seen by the system so far, if any. The system state calculator also takes the previous system state 346, $s_{N-1}$, into account. The previous system state is stored in a state register 360. When the system is processing the input data from a first time point, when N=0, for a patient, the system state register is empty. The system score calculator 350 uses the current system state to calculate a current risk score, $y_N$, which is an interim score based solely on the input data from $t_0$ to $t_N$. Once the current risk score has been calculated, the current system state, $s_N$, is stored in the state register 360, replacing the previous system state, $S_{N-1}$, having been temporarily stored in a delay 370. After the current score has been calculated, the input units subsequent to N are presented to the input circuit 110 and processed in order.

In an embodiment of the invention, for each new input data unit the system state calculator 330 calculates a new system state using the input units remaining in the sequence of input units 220 until the sequence of input units is exhausted. The current risk score obtained after the final input unit has been presented to the system is the risk score and is provided via the output circuit 150. This can be provided as a visual, textual, graphical or audio output. The parameters for the model, w, which comprise of parameters in the input data encoder 310, $w_x$, the time stamp encoder 320, $w_t$, system state calculator 330, $w_y$, and the score calculator 350, $w_s$, are learned during the process to train the machine learning model 230 in the CADx system.

The mathematical operations used by the score calculator 350 to transform the current system state 345 into a score, $y_N$, can be written as follows:

$$y_N = f s_N ; w_s \qquad 3.1$$

Since the system state at $t_N$ 330 contains the information regarding all the input units that the system has seen since the first time point $t_0$, the output risk score 140 corresponds to the risk considering the input sequence from the $0^{th}$ to the $N^{th}$ input data unit. Since the machine learning utilises its state after the previous input, $s_{N-1}$, it is referred to as a recursive neural network. Recursive neural networks are used in the domain of natural language processing. The system state calculator 230 of this invention is different to recursive neural networks typical in other machine learning applications because it operates in a scenario where the temporal data comes in variable time intervals. The setting of assessing the lung disease risk of a pulmonary nodule, a typical time interval between subsequent studies can range from a few days to a year or even several years, possibly upto three years. Furthermore, the assessment of a single case can consist of one, two or more studies. Therefore, the recursive network in the machine learning model 230 needs to account for the temporal dimension of the data explicitly, and hence the usage of an encoder for temporal information 320 which produces the timestamp descriptor 325.

Example of the Physical Implementation of the Model

Figure 3:
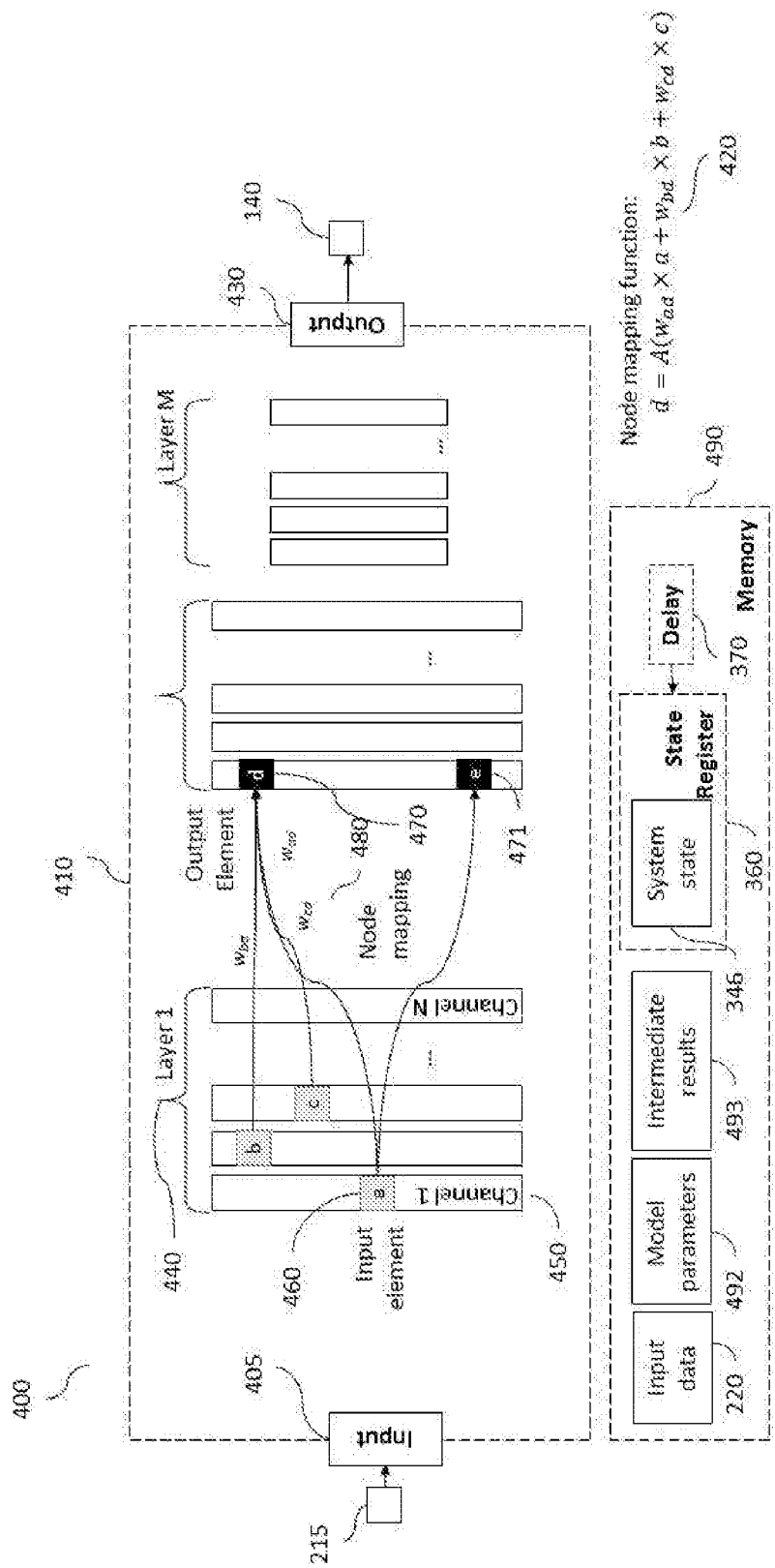
FIG. 3 shows the type machine learning model 230 used by the CADx system for unstructured temporal data.
Figure 4:
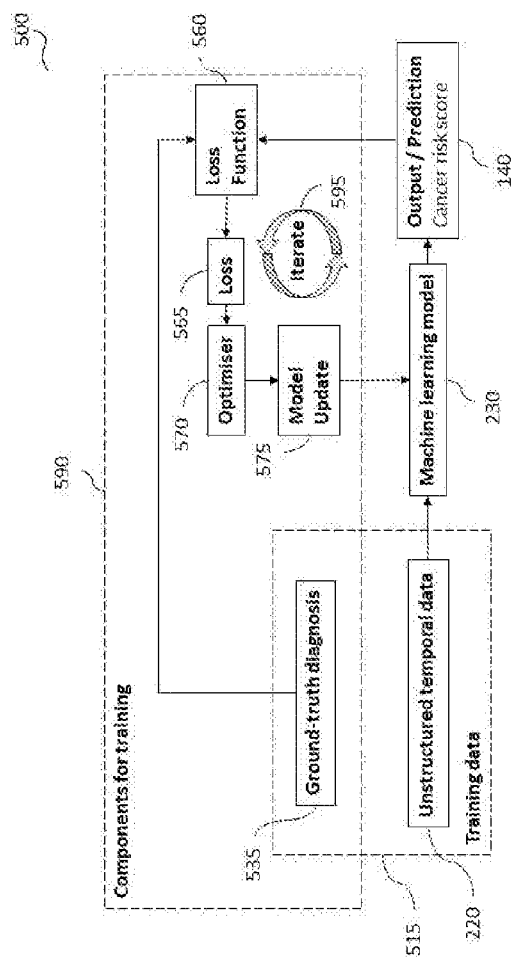
FIG. 4 shows an example of the training process for the CADx system according to an embodiment of the invention.

Referring now to FIG. 3, the type machine learning model 230 used by the CADx system for unstructured temporal data 200 may be, for example, the illustrated neural network 410, according to examples of the present invention. In some examples, the machine learning model 230 in the CADx system for temporal data 200 may comprise a neural network 410, which applies a series of node mappings 480 to the input data provided by the input circuit 110 to an input 405, which ultimately resolves into an output 430 consisting of one or more values, from which at least one of the values is used by the CADx system 200, for example a lung cancer risk score 140. The input layer comprises of the value in a data input unit 215 and includes the intensities of the input medical image 111, possibly in combination with clinical parameters 112 such as patient age and sex, and the result of relevant tests such as biomarkers 113, e.g. a test for a gene mutation associated with an increased risk of cancer, and the time stamp 214.

In an embodiment of the invention, the example neural network 410 comprises of a consecutive sequence of at least one network layers e.g. layers in 440, each of which consists of a series of at least one channel 450. There is no maximum limit on the number of channels in each layer, and the number of channels can vary between layers. The channels 450 are further divided into at least one input elements 460 Channels 450 can have varying numbers of inputs 460, and input elements 460 can be repeated in a channel 450. In this example, each input element 460 stores a single value, if more values are needed to be stored then more elements will be added to the channel 450. Some or all input elements 460 in an earlier layer are connected to the elements in a later layer by node mappings 480 Elements in layer 1 can connect to any subsequent layer. In this invention, there is recursion which means elements from later layers connect to earlier layers, but only via a state register 360 and a delay 370, which delays the use of these inputs until a new input is supplied} Elements 460 are connected between layers in the sense that the later element multiplies the value in the earlier element by a weight. This is the same for connections between all layers or can this be varied? For example layer 1 can connect to multiple subsequent layers. At least one connection is required between layers. Unconnected, i.e. zero weight, elements serve no purpose and would normally be discarded.

The weight is initially modified during the training process. Once training is complete it is fixed. The collection of weights in the node mappings 480, together, form the model parameters 492. For each node mapping 480, the elements in the earlier layer are referred to as input elements 460 and the elements in the output layer are referred to as the output elements 470. An element may be an input element to more than one node mapping, e.g. 460, but an element is only ever the output of one node mapping function 420 e.g. 470 stores the result of a node mapping function that takes elements a, b and c as inputs, and 471 stores the result of a node mapping function that only takes element a as an input.

In order to calculate the output 430 of the neural network 410 the system first considers the input data as the earlier layer. The layers to which the earlier layer is connected by a node mapping function 420 are considered in turn as the later layer. The value for each element in later layers is calculated using the node mapping function 420 in equation 4.1, where the values in the input elements 460 are multiplied by their associated weight in the node mapping function 420 and summed together.

Node mapping function 420:

$$d = Aw_{ad} \times a + w_{bd} \times b + w_{cd} \times c \quad \quad 4.1$$

The result of the summing operation is transformed by an activation function 'A' and stored in the output element 470 The neural network 410 now treats the previously considered later layers as the earlier layer, and the layers to which they are connected as the later layers. In this manner the neural network 410 proceeds from the input layer 440 until the values in the output 430 have been computed.

In some examples of the invention, the input data encoder 310, the time stamp encoder 320, the computation of the system state 230 and the score calculator 250 will each correspond to layers within the neural network. In layers where recursive computations are required, node mappings will link input elements 460 within the system state stored in the state register 360 to the appropriate output element 470. Once the output 430 has been calculated, further computations are performed that are associated with node mappings that link input elements in the rest of network to output elements in the stored system state. In this way the system state for the current time point is made ready for computing the score when the input corresponding to the next time point is provided.

In some examples of the invention, the large number of parameters used in the neural network may require the device to include a memory 490. The memory 490 may be used to store input data 220, the model parameters 492, intermediate results of the node mappings 593, and the previous system state 346.

In some examples of the invention, another neural network can comprise the CADx system, which may differ from the neural network in the CADx system for temporal data 200 in architecture but still operate using the same principles. Hence, while the above description of a neural network refers to the CADx system for unstructured temporal data, a skilled artisan will readily appreciate that an analogous approach can be used to construct a CADx system, such as the CADx system 200 in FIG. 2.

Those skilled in the art will readily appreciate that the CADx system for temporal data 200 can be implemented as a hardware device, a software package in a general-purpose computer, or on a firmware device such as a DSP.

Example of Training the Machine Learning Model

The process of determining the model parameters 492, w, of the neural network is the network training. An example of the training procedure is shown in FIG. 3. In examples of the invention, the neural network 410 may be trained using a set of input data sequences 220 from patients with their associated ground-truth lung cancer diagnosis 535, which constitutes the training data 515. The specific items required within the input data 215 that make up the input data sequence 220 are defined when the model is designed, and before training. For example, it can be medical images only 111 and a time stamp associated with each medical image 214, or a medical image 111 plus biomarkers 113 and timestamp 214. Different examples of the invention can use different items in the input data.

In some examples of the invention, the training of the neural network 410 may entail repeatedly presenting at least one set of input data sequences of the training data 515 to the neural network 410, in order to obtain the estimated risk score 140, for example by following the process 500 with training components 590. In some examples of the invention, the difference between the estimated output 140 and the ground-truth diagnosis may be computed using a loss function 560 which computes a loss value 565 which is chosen to measure how accurately the model predicts the labels given the associated data. In some examples of the invention, an optimiser e.g. 570 running an optimization algorithm may be used to reduce the loss 565, i.e. improve the model's performance, by measuring how much each model parameter contributed to the loss, and using the information to update the model parameters 575 in such a way as to reduce the loss 565. Each such modification is referred to as an iteration 595. After enough iterations, the neural network 410 can be used to estimate the cancer risk score for novel input data sequences.

Additional Training Details: Artificially Increasing the Amount of Unstructured Temporal Data Sequences Available for Training Training a neural network with many parameters requires large amounts on training data, which is particularly scarce and expensive in the medical domain. Artificial data augmentation techniques are commonly used to reduce the amount of novel data required by deriving new data samples from existing ones by applying a set of data transformations. The form of these transformations will depend on the type of data being use and the task that the neural network will perform. In addition to standard methods of augmentation, such as random perturbations in geometry and intensity, in some examples of the machine learning model 230 for the CADx system for unstructured temporal data 200, the training includes the derivation of novel unstructured temporal data sequences 220 from existing ones in the training data 515 by sampling a subset of the input data units For example, assuming we have N input data units available in a real sequence, both the size of the subset of units and the members of the subset are chosen randomly, resulting in a new sequence of length between 1 and N time points. Likewise, the training of some examples of the machine learning model 230 include the creation of novel unstructured temporal data sequences 220 by randomly perturbing the time stamps 214 of each input unit 215 in the training data 515. For example, such artificial alteration of the time stamps can take the following form:

$$t_N' = \operatorname{argmax} 0, t_N + n0, \sigma \quad \quad 5.1$$

Where $t_n$ is the time associated to the time stamp 214 of the $N^{th}$ input unit in the unstructured temporal sequence 215, and $n0, \sigma$ is a normal distribution with zero mean and standard deviation $\sigma$, which is chosen in proportion to $t_N$ such that the new time $t_N'$ reflects the variabilities than normally occur in the data. For example, the variability in time stamps for follow-up studies scheduled for one month later will be less than those scheduled for 6 months later.

Figure 5:
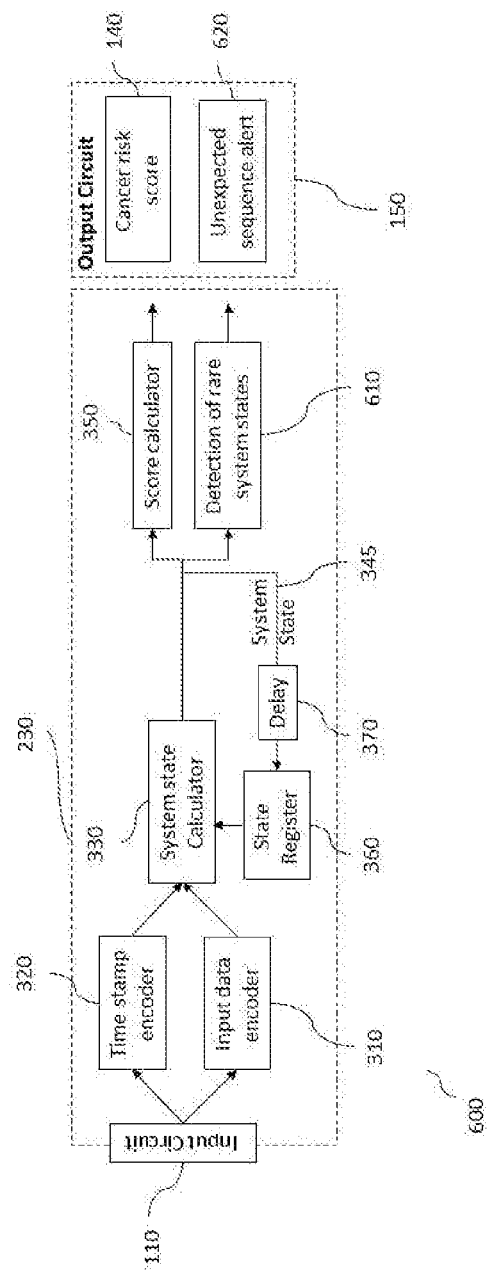
FIG. 5 shows an example of an embodiment of the CADx system of this invention with an alert mechanism.

Additional Functionality: Alerting the User of Sequences That Do Not Follow an Expected Temporal Profile Using the temporal information in a sequence of patient studies allows an embodiment of the invention to have a mechanism to flag sequences that do not follow an expected temporal evolution profile. This can be due to several reasons, including the case being clinically rare, as well as errors in the input data e.g. a study does not belong in the sequence, or is technically flawed. Whatever the reason, it is important to alert the managing clinician of a significant divergence from the expected progression of a case. A CADx system incorporating this alert mechanism is illustrated in FIG. 5, where it complements the cancer risk score 140 with an output 620 that indicates that an input sequence of studies diverges significantly from examples the machine learning model 230 has previously encountered in the training data.

The core of the alerting functionality is a module for the detection of rare system states 610. In an example of the CADx system with detection of unexpected temporal sequences, the module for the detection of rare sequences 610 is based on a statistical model able to evaluate the likelihood of a system state 345 and produce the unexpected sequence alert 620 when the likelihood value is below certain threshold. This is described in the following equation:

$$\text{alert}=[L(s;\theta)<\rho] \quad\quad\quad 6.1$$

Where $L(s; \theta)$ is the likelihood of the system state $s_N$ 345 under a probabilistic model with parameters $\theta$, $\rho$ is the threshold indicating the likelihood below which the alert is fired, and the notation [.] indicates a binary outcome.

In an embodiment of the invention, some examples of the module for the detection of rare sequences 610, the parameters $\theta$ of the likelihood function $L(\theta)$ in equation 6.1 are derived by fitting the probabilistic model to a representative set S of system states obtained from processing the training data sequences 515 with the machine learning model 230 of the CADx system for unstructured temporal data 200. In some example implementations, the fitting of the probabilistic model to the data set S in order to obtain the parameters $\theta$ is done with a standard expectation-maximization algorithm. In some examples of the module for the detection of rare sequences 610, the likelihood function $L(\theta)$ takes the form of a Gaussian Mixture Model GMM:

$$L(s;\theta=\{\mu,\sigma,\alpha\})=\Sigma_{k=1}^{K}\alpha_k Ns;\theta_k=\{\mu_k,\sigma_k\} \quad\quad 6.2$$

Where K is the number of Gaussian distributions components in the mixture model, in which $k^{th}$ component has a mean $\mu_k$, standard deviation $\sigma_k$ and contributes towards the mixture model with a weighting factor $\alpha_k$.

As described, the invention provides for the following features:

A CADx system for lung cancer risk scoring that takes unstructured temporal data as input. The term unstructured indicates that the input data that encountered in the typical clinical management of lung nodules, where the number of input data points, as well as the time interval between them is variable and not-known in advance.

The time stamp encoder 320 which enables machine learning model 230 for a CADx system for lung cancer risk 200 to operate on unstructured temporal data.

The method to artificially increase the amount of unstructured temporal sequences in the training data 515 by sampling data points from the existing training sequences.

The method to artificially increase the amount of unstructured temporal sequences in the training data 515 randomly perturbing the time stamps 214 of each input unit 215 of existing temporal sequences in the training data 515.

The module 610 to detect rare systems states which allows a CADx system for unstructured temporal to alert the user if an input sequence diverges from what is expected in the natural evolution of a lung nodule.

As described in an embodiment of the invention, the CADx system 200 for lung disease risk score takes unstructured temporal data as input. The term unstructured indicates that the input data that encountered in the typical clinical management of lung nodules, where the number of input data points, as well as the time interval between them is variable and not-known in advance. In a further preferred embodiment of the invention the time stamp encoder 320 enables the machine learning model 230 for the CADx system 200 for lung disease risk to operate on unstructured temporal data.

In a preferred embodiment of the invention, the method allows for the artificial increasing of the amount of unstructured temporal sequences in the training data 515 by sampling data points from the existing training sequences.

Further preferably, the method of an embodiment of the invention can artificially increase the amount of unstructured temporal sequences in the training data 515 by randomly perturbing the time stamps 214 of each input unit 215 of existing temporal sequences in the training data 515.

In a further embodiment of the invention module 610 can detect rare systems states which allows a CADx system 200 for unstructured temporal to alert the user if an input sequence diverges from what is expected in the natural evolution of a lung nodule.

As described above, the system and method of this invention can be applied where there is a need to assess the risk of lung cancer directly from standard diagnostic exams or medical images such as CT scans, or other imaging modalities.

Specific cases include.

As part of decision support system used within a hospital or clinic that cares for patients with pulmonary nodules, where the managing clinicians would like to get an independent assessment of lung cancer risk for the nodule present in a patient based on one or more imaging scans, such as a CT scan.

As part of a platform to track and monitor patients with pulmonary nodules, where this invention is used to assess the risk of cancer of a patient in the platform's database to help the clinician choose the appropriate clinical pathway to follow. The invention is particularly relevant where the risk of cancer needs to be updated as new information becomes available.

As part of a system that automatically parses large databases of CT scans of patients looking for nodules, e.g. within a large hospital system, which are then automatically assessed for risk of cancer in order to identify high-risk cases that must be prioritized for clinicians.

Although examples of the invention have been described with reference to the CADx system being used to assist in the interpretation of chest images and lung nodules, it is envisaged that the concepts described herein may be employed beyond this area of the human body. In other examples, it is envisaged that the concepts may be applied in any medical application where it is important to consider other aspects of the clinical context, such as economic and patient preferences, where one or more medical images are being analysed.

Although examples of the invention have been described with reference to measuring lung disease risk that reviews images for a specific patient, it is envisaged that the concepts described herein may be employed in an automated system that examines all medical images stored on, say, a hospital database, in order to identify risk scores for other patients who, in the absence of other information, can be assumed to be of greater risk of lung disease.

Although examples of the invention have been described with reference to a CADx device, it is envisaged that the improved lung disease risk measure may be employed by a nodule clinic NC manager or pulmonologist in assessing a nodule's malignancy. For example, the nodule may be of intermediate size and may appear to the NC manager to be potentially suspicious. It may also be that a lung disease risk score, is of intermediate risk, i.e. it concurs that the nodule is not obviously benign. As a consequence, the patient may be required to attend a follow-up check after a shorter interval, where the nodule is found to have grown. Subsequent biopsy could identify the nodule as being a progressive squamous cell carcinoma. Thanks to the shortened follow-up time, the cancer is identified early enough that a lobectomy procedure cures the patient, because further growth and secondary cancers never have a chance to occur.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system. Therefore, some examples describe a non-transitory computer program product having executable program code stored therein for receiving at least one input medical image of a patient in which the patient's lungs are visible.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media e.g., CD ROM, CD R, etc. and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing running program or portion of a program, current program values and state information, and the resources used by the operating system to manage the execution of the process. An operating system OS is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output I/O devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

We claim:

1. A method for providing a lung disease risk measure in a Computer Aided Diagnosis system comprising the steps of:
   receiving a plurality of inputs in an input sequence for a subject at an input circuit, each input comprising at least one image showing all or part of the lungs of a patient and a time stamp for the image, where the inputs are obtained at varying intervals;
   analysing the inputs using a machine learning model to assess temporal changes in the images using an input data encoder and a time stamp encoder, wherein the input data encoder identifies patterns in the input data and encodes the result of the input processing as an input data descriptor; and the time stamp encoder parses time information about the image as a vector $t_N$;
   wherein the output from at least one encoder is provided to a system state calculator, and the system state calculator encodes a summary of all the input data received at that time; wherein system state calculator is updated via a feedback system, to take account of data from successive images, where for each new input data the system state calculator calculates a new system state using input units remaining in the sequence of input units until the sequence of input units is exhausted;
   inputting the output of the system state calculator to a score calculator to calculate a risk score; and
   outputting the risk score from an output circuit indicating the lung disease risk for the subject, wherein the risk score is the risk score obtained after the final input unit has been presented to the system.

2. A method as claimed in claim 1, wherein the lung disease is lung cancer.

3. A method according to claim 1, wherein each variable interval between inputs is up to 3 years.

4. A method according to claim 2, wherein the variable interval between inputs is between 1-18 months.

5. A method according to claim 1, wherein the variable intervals between each input of the plurality of inputs are all different.

6. A method according to claim 1, wherein the system state calculator calculates the current risk score based on input data it has received between an initial starting point with zero input to the system state calculator and a point when at least one input of a plurality of inputs has been provided to the system state calculator.

7. A method according to claim 1, further comprising the step of: detecting a rare system state, and outputting an alert with the risk score to indicate the detected rare state.

8. A method according to claim 1, wherein the input image is one of: a CT image, an MRI image, a PET image, an X-ray image, an ultrasound image or a SPECT image.

9. A method as claimed in claim 1, wherein the input further comprises one of more of: biomarkers for the patient or clinical parameters for the patient.

10. A method according to claim 9, wherein the biomarkers and clinical parameters comprise at least one of: patient age, patient sex, results of blood tests, results of lung function tests.

11. A method according to claim 1, wherein the machine learning model uses a neural network.

12. A method according to claim 11, wherein the neural network is a recursive neural network.

13. A method according to claim 1, wherein the output is an textual, visual or audio output.

14. A computer aided diagnosis lung disease risk measurement system comprising:
   an input circuit for receiving a plurality of inputs in an input sequence for a subject, each input comprising at least one image showing all or part of the lungs of a patient and a time stamp for the image, where the inputs are obtained at varying intervals;
   an analysis circuit comprising an input data encoder and a time stamp encoder for analysing the inputs using a machine learning model to assess temporal changes in the images using the input data encoder and a time stamp encoder wherein the input data encoder identifies patterns in the input data and encodes the result of the input processing as an input data descriptor; and the time stamp encoder parses time information about the image as a vector $t_N$;
   wherein the output from at least one encoder is provided to a system state calculator, and the system state calculator encodes a summary of all the input data received at that time;
   wherein system state calculator is updated via a feedback system, to take account of data from successive images, where for each new input data the system state calculator calculates a new system state using input units remaining in the sequence of input units until the sequence of input units is exhausted;
   said analysis circuit further comprising to a score calculator for receiving the output of the system state calculator to calculate a risk score;
   and an output circuit for outputting the risk score indicating the lung disease risk for the subject, wherein the risk score is the risk score obtained after the final input unit has been presented to the system.

15. A computer aided diagnosis system according to claim 14, further comprising: a circuit configured for the detection of rare system states to determine a rare system state and wherein the output circuit also comprised an alert mechanism, to provide an alert along with the disease risk output when the rare system state is determined.

16. A computer aided diagnosis system according to claim 15, wherein the circuit configured for the detection of rare system states evaluates the likelihood of a system state and compares this with a threshold level to determine the rare system state and to generate the alert.

* * * * *